(12) United States Patent
Wang et al.

(10) Patent No.: US 8,836,931 B2
(45) Date of Patent: Sep. 16, 2014

(54) DETECTION SYSTEM AND METHOD FOR ACQUIRING RESONANCE ANGLE OF SURFACE PLASMON

(75) Inventors: Kun Wang, Beijing (CN); Jinsong Zhu, Beijing (CN); Zheng Zheng, Beijing (CN); Jiangfeng Fan, Beijing (CN)

(73) Assignees: National Center for Nanoscience and Technology, China, Beijing (CN); Beihang University, Beijing (CN)

( * ) Notice: Subject to any disclaimer, the term of this patent is extended or adjusted under 35 U.S.C. 154(b) by 357 days.

(21) Appl. No.: 13/125,382

(22) PCT Filed: Oct. 28, 2008

(86) PCT No.: PCT/CN2008/001813
§ 371 (c)(1),
(2), (4) Date: Jul. 25, 2011

(87) PCT Pub. No.: WO2010/048742
PCT Pub. Date: May 6, 2010

(65) Prior Publication Data
US 2011/0285986 A1    Nov. 24, 2011

(51) Int. Cl.
*G01B 11/26*   (2006.01)
*G01N 21/55*   (2014.01)

(52) U.S. Cl.
CPC .................................. *G01N 21/553* (2013.01)
USPC ...... 356/152.1; 398/172; 436/518; 435/287.2

(58) Field of Classification Search
USPC ........................ 356/152.1; 398/172; 436/518; 435/287.2
See application file for complete search history.

(56) References Cited

U.S. PATENT DOCUMENTS

| | | | | |
|---|---|---|---|---|
| 5,222,129 A | * | 6/1993 | Bonvallet et al. | 379/395.01 |
| 5,852,636 A | * | 12/1998 | Mathieu et al. | 375/272 |
| 6,339,471 B1 | * | 1/2002 | Morita | 356/401 |
| 6,457,178 B1 | * | 9/2002 | Slim | 725/127 |
| 6,982,819 B2 | * | 1/2006 | Sawin et al. | 359/245 |
| 7,317,519 B2 | | 1/2008 | VanWiggeren et al. | |
| 7,684,024 B2 | | 3/2010 | VanWiggeren et al. | |
| 7,948,634 B2 | * | 5/2011 | Bankhead et al. | 356/497 |
| 7,968,474 B2 | * | 6/2011 | Martin et al. | 438/800 |
| 2004/0155309 A1 | * | 8/2004 | Sorin et al. | 257/433 |
| 2005/0012932 A1 | * | 1/2005 | Yamada et al. | 356/445 |
| 2006/0173359 A1 | * | 8/2006 | Lin et al. | 600/478 |
| 2008/0198383 A1 | | 8/2008 | Weibel | |

FOREIGN PATENT DOCUMENTS

| | | |
|---|---|---|
| CN | 1766575 A | 5/2006 |
| CN | 101113887 A | 1/2008 |
| JP | 2001-255267 A | 9/2001 |

* cited by examiner

*Primary Examiner* — Isam Alsomiri
*Assistant Examiner* — Samantha K Abraham
(74) *Attorney, Agent, or Firm* — Drinker Biddle & Reath LLP

(57) ABSTRACT

The present disclosure provides a detection system for acquiring the SPR angle, including a modulatable SPR sensor to be detected; an incident light source apparatus; a photoelectric detector; a narrowband filter system; a modulated signal source for generating an alternating current signal that is used to modulate said modulatable SPR sensor; and a data processing system for recording the corresponding relationship between the incident angle and the intensity of the filtered reflected light and further obtaining the resonance angle of said modulatable SPR sensor. The present disclosure also provides a corresponding detection method for acquiring the SPR angle.

10 Claims, 4 Drawing Sheets

DETECTION SYSTEM AND METHOD FOR ACQUIRING RESONANCE ANGLE OF SURFACE PLASMON

CROSS-REFERENCE TO RELATED APPLICATIONS

This application is a national stage application, under 35 U.S.C. §371, of PCT/CN2008/001813, filed Oct. 28, 2008.

TECHNICAL FIELD

The present invention relates to the field of sensors and sensing technology, in particular to a detection system used in the surface plasmon resonance sensor technology and a method for acquiring the surface plasmon resonance angle.

BACKGROUND ART

Surface Plasmon (abbreviated as SP) is a vibration mode that is formed by the collective oscillation of metal surface electric charges and propagates along an interface between a metal and a dielectric; a surface plasmon wave is present on the interface of two materials with opposite signs of dielectric constants (generally being a metal and a medium). Surface Plasmon Resonance (abbreviated as SPR) is a physical optical phenomena that is a surface plasmon oscillation phenomena of an optical wave generated on the interface of two mediums with opposite signs of dielectric constants (such as the interface of a metal and a medium). The energy of an incident optical wave can be coupled into the plasmon wave using the method of prism-coupling Attenuated Total Reflection (abbreviated as ATR): when a linear polarization surface optical wave with the electric component parallel to the incident plane is incident on the interface in a specific angle, the wave vector of the surface plasmon wave matches that of the evanescent wave, which is parallel to the interface, the energy of the incident light is coupled into the surface plasmon wave. At this specific angle, the energy of the reflected light decreases dramatically, forming a downward sharp peak, i.e., a SPR is generated. At this moment, the corresponding specific incident angle is called as surface plasmon resonance angle (abbreviated as SPR angle). Since the generation of the SPR closely relates to the refractive index and thickness of the medium contacting the metal, the SPR can be used as a sensor to detect the refractive index of different solutions and the biochemical reaction happening at the metal interface.

A SPR sensor plays an important role in many aspects of detection due to its high sensibility and real-time detection ability. At present, the angle scan detection method is the most common detection method adopted by the SPR sensor. This method can be used to detect an SPR angle to thereby obtain a series of important parameters, such as the dielectric constant of the detected medium on the surface. Therefore, the determination of the SPR angle is one of the key technologies for the SPR sensor.

Nowadays, according to the typical angle scan detection method, a light source having a fixed wave length is used, said incident angle is changed by using a focus light beam distributed in a certain angle or by using a rotary table, to obtain the intensity of the reflected light under all incident angles, and thereby obtaining an angle position corresponding to the peak value of the reflected light intensity curve (this peak value refers to the minimum value of the intensity of the reflected light, which is called as SPR peak), the SPR angle is then determined according to the position of said peak value. However, due to the limitation to the instruments, the interval of angle scan cannot be shortened unlimitedly, the intensities of the reflected light actually measured are some discrete values, while the resonance peak including the SPR angle is not symmetrical, moreover, during the process of detection, the offset of the resonance angle caused by the variation of dielectric constants of the detected object is usually very small, all these bring a big problem to an accurate determination of said resonance angle, currently the methods of processing the obtained data are mainly as follows: centroid method, multinomial fitting, dynamics baseline, etc., these methods can be used to obtain the relatively precise data concerning resonance angle, however, these data are obtained on the basis of acquiring experiment data and then processing said data experience in a complex way using the abovementioned methods, therefore, the offsets and errors occurring in real time during the process of experiment will affect the final result; the data processing algorithm to be realized is quite intricate, complex hardware or software is required, thus limiting the lowering of system cost; in addition, there exist certain errors in different processing methods, due to the influence of human factor such as setting parameters during data processing, it is not sure to reflect an exact experiment result actually, so there is an urgent desire for a detection method which is able to acquire an SPR angle more conveniently, quickly and accurately during the process of experiment.

SUMMARY OF THE INVENTION

The object of the invention is to overcome the disadvantages in the prior art and to provide a SPR detection system capable of acquiring the SPR angle accurately and reliably without complex data processing algorithm involved, and a detection method capable of acquiring the SPR angle by using said system.

According to one aspect of the present invention, it proposes a detection system capable of acquiring the SPR angle accurately.

As shown in FIG. 1, the system comprises an incident light source device for generating a light with a single wavelength and the polarization state being a transverse magnetic wave ("TM wave"), a modulatable SPR sensor to be detected, a modulated signal source, a photoelectric detector for receiving the reflected light, a narrowband filter system and a data processing system;

The output of said modulated signal source is connected to the modulated input of the modulatable SPR sensor, the input of said narrowband filter system is connected to the output of the photoelectric detector, the output of said narrowband filter system is connected to the input of the data processing system; said modulated signal source can generate an alternating current signal having a certain frequency and cycle.

In the above system, said incident light source device comprises a laser light source and a light polarization control means, said light polarization control means could be polaroid, Glan prism, polarizing beam splitter, or any combination thereof.

In the above system, said modulatable SPR sensor is able to excite a surface plasma resonance effect and its generation condition for the SPR effect can be changed by the modulated input signal.

In the above system, said narrowband filter system refers to a system allowing the pass of the signals near a specific frequency component in the input signals in a manner of hardware or software. The pass band width is much smaller than this specific frequency, for example, a passive narrowband filter, a phase-locked amplifier, or a soft-and hardware system consisting of an analog-to-digital converter and a digital signal processing filter.

In another aspect, the present invention further provides a method of accurately acquiring the SPR angle based on the aforesaid SPR detection system, comprising the steps of:
(1) forming a layer to be detected on the surface plasmon function layer of said sensor;
(2) directing the light emitting from the light source incident on said modulatable SPR sensor via the light polarization control means, and converting the reflected light into electrical signals by the photoelectric detector, said electrical signals being processed by the narrowband filter system and data processing system;
(3) modulating said modulatable SPR sensor by using an alternating current signal with a certain frequency generated by the modulated signal source;
(4) setting the passband central frequency of the narrowband filter system to the same frequency as that of the output signal of the modulated signal source;
(5) recording the corresponding signal output of the narrowband filter system by the data signal system under different incident angles, thereby acquiring the incident angles and the intensity of the reflected light passing through the filter; and
(6) according to the curve showing the relationship between said obtained incident angle and the intensity of the filtered reflected light, obtaining a position where the intensity of said reflected light is zero in the curve via straight line fitting, the incident angle corresponding to this position being representing the resonance angle.

In step (3) of the above technical solution, said alternating current signal comprises a periodic alternating current signal with a certain frequency, such as a sine signal, a cosine signal, a triangular signal, and a square wave signal and etc.

In the above technical solution, a curve showing how the modulated intensity varies with the incident angle is obtained from the filter system, and then is recorded and processed.

Compared to the prior art, the present invention has the following technical effects:

The present invention sets forth a method capable of accurately measuring the resonance peak position of the surface plasmon. It differs from the traditional data processing method in that the latter uses complex mathematical methods to process the directly measured resonance peak of the surface plasmon that has a complex shape, thus obtaining the resonance peak position or the offset. This invention uses a tunable sensor to modulate the resonance peak of the surface plasmon and filter the detected modulated signal to obtain a detection signal that has a very simple shape, from which the information related to the position or the offset of the resonance peak can be obtained accurately without complex mathematical or software data processing. In this way, the hardware devices such as a signal source and a filter can be used to realize a real time detection and accurately obtain the position of the resonance peak in real time, thereby greatly simplifying the process of detection and data processing, saving the detection time, reducing the system cost and the complexity degree, and improving the detection efficiency.

DESCRIPTION OF DRAWINGS

The implementation of the invention is explained in detail in combination with the accompanying drawings, wherein.

SPECIFIC EMBODIMENTS

Examples

This example proposes a new system and method for detecting the SPR angle on the basis of the PCT application "Waveguide Coupling Surface Plasmon Resonance Sensor, the Structure and Manufacturing Method of the Sensor Array, Measuring System Using Said Sensor or Sensor Array and Measuring Method thereof" (the application No.: PCT/CN2007/002664). The aforesaid PCT application designs a parallel plate waveguide SPR detection structure using the electro-optic, magneto-optic and acousto-optic materials as functional layers, thereby forming a waveguide coupled surface plasmon resonance (abbreviated as WCSPR) sensor based on the electro-optic, magneto-optic and acousto-optic modulation modes and a sensor array thereof. For the WCSPR sensor using electro-optic, magneto-optic and acousto-optic materials as functional layers, the parameters of the modulated waveguide layer can be modulated through the modulation manners such as voltage modulation and magnetic field modulation so as to change the resonance angle of said WCSPR sensor. This PCT application (PCT/CN2007/002664) is combined into the present application as a whole for reference.

In the aforesaid PCT application, a direct current modulation is used to change the position of the waveguide coupled surface plasmon resonance peak. The change of the refractive index of the detected solution is determined through voltage scan; the present invention uses an alternating current signal to replace a direct current signal to modulate the waveguide coupled surface plasmon resonance peak. Compared to the integral translation of the resonance peak caused by the direct current signal, the modulation of the alternating signal results in a complete change to the shape of the waveguide coupled surface plasmon resonance peak. Under the shape of the waveguide coupled surface plasmon resonance peak provided by the invention, a more accurate position of the resonance peak can be obtained, and the operation is easy and convenient. Below is the further description of the present invention, taking for example of the modulation of the waveguide coupled surface plasmon resonance peak by the alternating voltage based on electro-optic effect.

Figure 1:
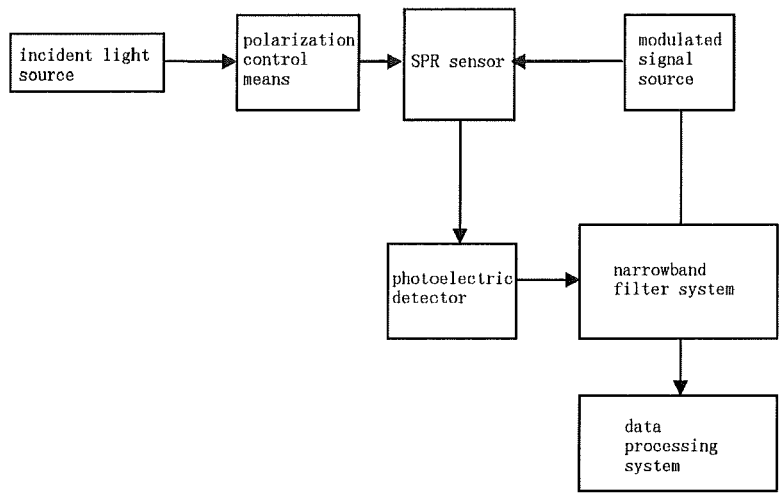
FIG. 1 is a block diagram illustrating the principle of the detection system set forth in the present invention.
Figure 2:
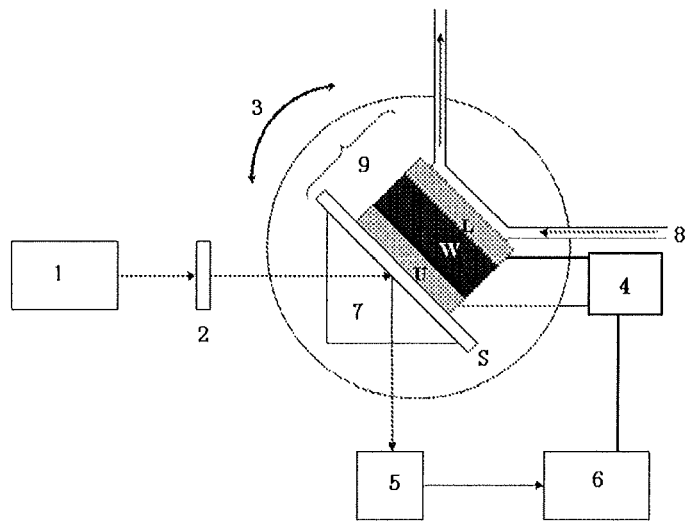
FIG. 2 is a schematic diagram of experiment devices set forth in the present invention, wherein each part will be described specifically in the following text.

As shown in FIG. 2, the present invention sets forth a system of sensing and detecting the waveguide coupled surface plasmon resonance based on the electro-optic effect, said system mainly comprises the following components: 1. a single-wavelength laser source with a wavelength of 980 nm used in this example; 2. a polarizer of TM polarization for ensuring that the incident light can excite a SPR; 3. a rotary table for changing the angle incident on the prism coupler to seek for a resonance angle; 4. a signal generator for providing a modulation voltage for the waveguide coupling surface plasmon resonance sensor 9, and providing a reference signal for narrowband filter system 6 (which is a phase-locked amplifier in this example); 5. a photoelectric detector for collecting the modulated reflected light signal as the detected signal and providing the latter to the narrowband filter system 6; 7. a coupling device, here a prism is used in the present invention, this prism couples the light into sensor 9; 8. a microflow duct made of polydimethylsiloxane ("PDMS") and is injected the detected solutions of different concentrations to verify the present invention; chip 9 includes a basic structure of a multi-film WCSPR sensor, mainly consisting of three parts: S represents a substrate that is made of ZF7 glass whose refractive index is 1.7761@980 nm, the same as that of the prism; U and L represent the upper metal layer (a metal layer in contact with the prism coupler, which is a gold thin film in this example) and the lower metal layer (a metal layer in contact with the detected material, which is a gold thin film in this example), respectively, both being prepared by ion-source-assisted evaporation deposition with the thicknesses of 30 nm and 35 nm respectively, the refractive index of gold is 0.185145+6.1504i@980 nm; W represents a waveguide layer, an electro-optic waveguide layer is formed by spin coating of an organic material having an electro-optic effect and a commercially available Polycarbonate, the thickness thereof is 2500 nm, the refractive index is 1.60388@980 nm; the detected solution used in this example is a D-dextrose water solution with different concentrations.

The reflected intensity of a five-layered structure, consisting of the prism, the detected material and the WCSPR waveguide structure, can be obtained from Fresnel equation, as shown in equation (1), wherein parameters 1-5 represent the prism, the upper layer gold U, the medium waveguide layer W, the lower layer gold L and the detected material layer respectively, R represents the reflected intensity of the system, $K_{zi}$ represents the component of the wave vector that is parallel to the interface in the $i^{th}$ layer, $n_i$ represents the refractive index of the $i^{th}$ layer, $d_i$ represents the thickness of the three-layered structure of WCSPR, $\lambda$ is the incident wavelength, and $\theta$ is the incident angle.

$$R = |r_{0,4}|^2 \qquad (1)$$

$$r_{i,4} = \frac{r_{i,i+1} + r_{i+1,5} e^{2jd_{i+1}k_{zi+1}}}{1 + r_{i,i+1} r_{i+1,5} e^{2jd_{i+1}k_{zi+1}}}$$

$$(i = 2, 1, 0; j = 1\sqrt{-1})$$

$$r_{i,i+1} = \frac{x_{i+1} - x_i}{x_{i+1} + x_i} (i = 0, 1, 2, 3)$$

$$x_i = \frac{n_i^2}{k_{zi}} (i = 0, 1, 2, 3, 4)$$

$$k_{zi} = \sqrt{\left(\frac{2\pi}{\lambda}\right)^2 n_i^2 - k_{0x}^2} \quad (i = 0, 1, 2, 3, 4)$$

$$k_{0x} = \frac{2\pi}{\lambda} n_1 \sin\theta$$

If the alternating current voltage V provided by the signal generator is applied across the upper and lower metal layers, and is also provided to the phase-locked amplifier as a reference signal. The modulated reflected intensity thus obtained by the phase-locked amplifier is not only a function of the incident angle $\theta$, but also a function of the modulation voltage V:

$$R = R(\theta, V) \qquad (2)$$

The periodic modulation voltage V (here is a sine modulation voltage in this example) with a certain frequency generated by the modulated signal source can be represented as:

$$V = V_0 \sin(\omega t + \alpha) \qquad (3)$$

Wherein $V_0$ represents the amplitude of the modulation voltage, $\omega$ is the frequency, $\alpha$ is the initial phase which is zero in this example. Below can be proven that the modulation voltage only needs to be a periodic alternating current signal with a certain frequency, but is not limited to be a sine modulation signal. In the frequency space, the Fourier transform of the modulation intensity can be represented as:

$$F_{R(\theta, V_0 \sin(\omega_0 t))} = \left[ R(\theta, 0) + \frac{V_0^2}{4} \frac{\partial^2 R}{\partial V^2} \bigg|_{V=0} + \frac{V_0^4}{64} \frac{\partial^4 R}{\partial V^4} \bigg|_{V=0} + \ldots \right] + \qquad (4)$$

$$\left[ \frac{V_0}{1!} \frac{\partial R}{\partial V} \bigg|_{V=0} + \frac{V_0^3}{8} \frac{\partial^3 R}{\partial V^3} \bigg|_{V=0} + \frac{V_0^5}{192} \frac{\partial^5 R}{\partial V^5} \bigg|_{V=0} \ldots \right] *$$

$$i * \frac{\sqrt{\pi}}{2} \delta(\omega - \omega_0) + \sum_{j=2}^{\infty} A_j * \delta(\omega - j\omega_0) + \ldots$$

Equation (4) $A_j$ represents the coefficient of the coefficient $\delta(\omega - i\omega_0)$, the expression thereof is the sum of the derivatives of different orders of R to modulation voltage V, similar to the coefficients of the first and second items in the right side of the equation. The intensity obtained by the narrowband filter (the instrument used in this example is a phase-locked amplifier) is an intensity of a signal which matches the reference signal frequency. In the above equation, the modulated reflected intensity I is:

$$I = \sum_{n=0}^{\infty} \frac{V_0^{2n+1} \partial^{2n+1} R}{4^n n!(n+1)! \partial V^{2n+1}} \bigg|_{V=0} \qquad (5)$$

$$= V_0 \frac{\partial R}{\partial V} \bigg|_{V=0} + \frac{v_0^3}{8} \frac{\partial^3 R}{\partial V^3} \bigg|_{V=0} + \ldots$$

$$\frac{\partial R}{\partial V} = \frac{\partial R}{\partial \theta} \frac{\partial \theta}{\partial V} \qquad (6)$$

Figure 3:
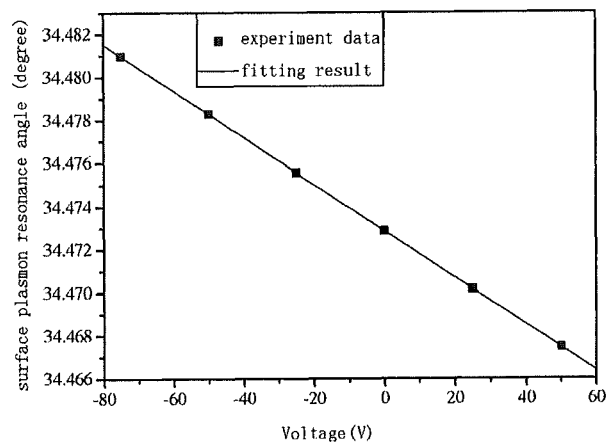
FIG. 3 illustrates the effect of the voltage on the resonance angle based on the traditional angle scan.

From equation (5), the relationship between the alternating current modulation intensity and the traditional angle reflected intensity can be established. In expression (5), compared to the first item in the right side, the second item in the right side and all the items thereafter are infinitely small and can be ignored. From FIG. 3 it can be seen that when the detected material is air, angle $\theta$ of the resonance peak is in a linear relation with the modulation voltage V, i.e., in equation (6) the differential of the angle to the voltage is a constant coefficient, so the alternating current modulated intensity I is determined only by the differential of R to $\theta$. In view of $\partial R/\partial \theta = 0$ at the peak of the WCSPR, the modulation intensity I is zero. Therefore, during the process of detection, the SPR angle can be obtained as long as the position of the zero on the alternating current modulated spectrum is obtained, thereby acquiring the relevant information of the detected material. This achieves a more accurate SPR angle than those methods like data fitting, and it is also a basic principle of the detection method recited in this invention.

Figure 4:
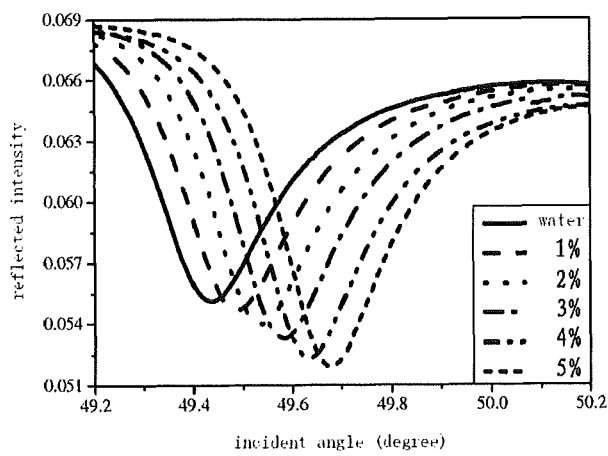
FIG. 4 illustrates a curve showing how the position of the resonance peak varies with the concentration of the detected solution based on the traditional angle scan.

The formulated detected solution of a certain concentration is filled to the surface of the lower layer gold via the microflow duct, FIG. 4 illustrates a curve of the reflected intensity varying with the incident angle in the solutions of different concentrations (refractive indices), given by the traditional SPR detection signal. It is found from this figure that with the increase of the dextrose concentration in the dextrose water solution, not only presents the position of the WCSPR peak angle a regular change, but also the depth of the resonance peak does.

Figure 5:
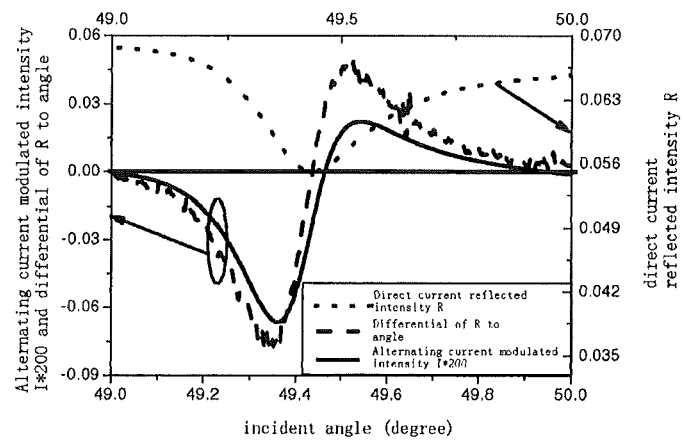
FIG. 5 illustrates a comparison of the intensity of an alternating current modulation and the differential of the reflected intensity in a traditional angle scan to the incident angle when the detected solution is fixed to a 1% glucose solution.

The detected solution is fixed to a 1% dextrose solution, the alternating current voltage provided by the signal generator not only is applied across the upper and lower metal layers, but also is provided to the phase-locked amplifier as a reference signal such that the central frequency of the phase-locked amplifier passband is in consistency with the modulated signal frequency, the phase-locked amplifier is used to obtain the modulating intensity under such situation. FIG. 5 illustrates the modulated intensity I (amplified by 200 times) and the differential of the angle-modulated reflected intensity to the incident angle. It can be found from this figure that both are quite similar to each other, except for a difference at the position of zero. The main reasons are as follows: the voltage modulation changes the refractive index variation of the waveguide layer; the refractive index variation of the waveguide layer not only changes the resonance angle, but also affects the depth of the resonance peak, then the differential of the reflection peak will result in the difference. However, this difference will not affect the measurement of the offset of the resonance peak, and the latter is a main physical quantity measured by the SPR detection system, therefore, said difference will not affect the detection result.

Figure 6:
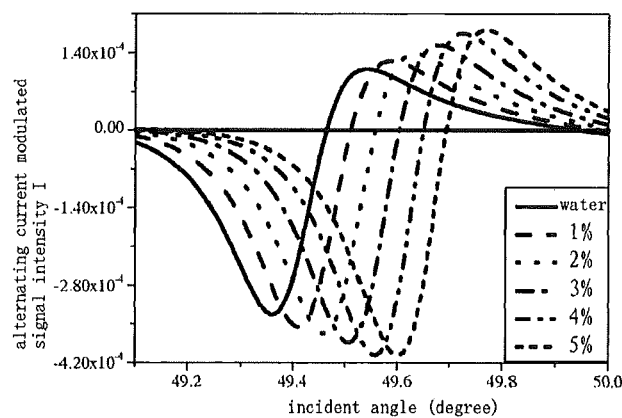
FIG. 6 illustrates a curve of the modulated intensity, obtained by using the detection method set forth in the present invention, varying with the concentration of the detected solution, and a variation curve of the position of the obtained resonance peak.
Figure 7:
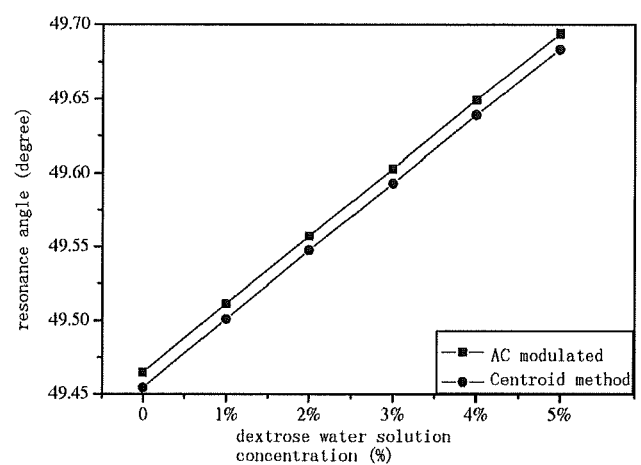
FIG. 7 illustrates a comparison of the angle variation curve of the present invention and that of the method of acquiring the resonance angle using the traditional centroid method.

Using the same detection method, FIG. 6 illustrates a curve of the alternating current modulated intensity varying with the incident angle under the dextrose solution of different concentrations, as well as a curve of the position of the resonance peak varying with the concentration as obtained under such situation, it is found that the resonance angle changes linearly with the concentration, which completely conforms to the traditional SPR detection theory. In order to compare the advantages and disadvantages between the angle scanning technologies recited in the present invention and the traditional technology and to detect the sensitivity, FIG. 7 illustrates a comparison between the resonance angle solved using the centroid method and the resonance angle obtained by the present invention. It is found from this figure that the present invention remains the sensitivity of the traditional angle scan detection method, and is easier and more convenient to obtain the information like the position of the resonance peak, compared to the centroid method.

It is worthy to note that although this example adopts the sensor system mentioned in "Waveguide Coupling Surface Plasmon Resonance Sensor Chip and Sensor Chip Array Thereof", those skilled in the art should understand that the method of the invention can also be applied to other SPR sensor systems that are able to tune the SPR peak. The alternating current modulated signal in this example is a voltage signal, however, other kinds of alternating current modulated source signal, like alternating current magnetic field can also be adopted.

In addition, it is already pointed out in the above text that the alternating current signal in this example adopts a sine wave, however, the invention is not limited to this, other periodic alternating current signals with a certain frequency, such as triangular wave, a saw tooth wave, or a square wave, can replace the sine wave in the present invention. This is because any alternating current modulated signal having a certain period can be developed into the sum of sine and cosine signals with a certain frequency by Fourier series. For example, f(t) is a non-sine periodic function, its period is T, the frequency and the angle frequency are f and $\omega$, respectively, which can be developed as follows using Fourier series:

$$f(t) = \frac{a_0}{2} + \sum_{n=1}^{\infty} (a_n \cos n\omega t + b_n \sin n\omega t) \tag{7}$$

In equation (7), each coefficient can be obtained from the following equations:

$$a_0 = \frac{2}{T} \int_{-\frac{T}{2}}^{\frac{T}{2}} f(t) dt \tag{8}$$

$$a_n = \frac{2}{T} \int_{-\frac{T}{2}}^{\frac{T}{2}} f(t) \cos n\omega t \, dt$$

$$b_n = \frac{2}{T} \int_{-\frac{T}{2}}^{\frac{T}{2}} f(t) \sin n\omega t \, dt$$

In combination of equations (7) and (8), it can be found that the developed series of the sine periodic function f(t) contain the sine component with a certain frequency, therefore, using the non-sine periodic function with a certain frequency as the modulation source of the invention can get the same conclusion as well, the difference only results from the difference in the resulting modulated intensity due to different amplitudes.

Finally, it should be mentioned that the embodiments in all figures are only used to explain the technical details of the invention but are not intended to construe a limitation. Although the present invention is described in detail with reference to its preferable embodiments, it will be understood by those skilled in the art that various changes in form and details may be made therein without departing from the spirit and scope of the invention as defined by the appended claims and their equivalents.

The invention claimed is:

1. A detection system for acquiring the SPR angle, comprising:
    a modulatable SPR sensor to be detected;
    an incident light source for generating a light with a single wavelength and the polarization state being a transverse magnetic wave that is incident on said modulatable SPR sensor;
    a photoelectric detector for receiving the reflected light and converting the light intensity into electrical signals;
    a narrowband filter system for filtering the output of said photoelectric detector to obtain the light intensity value;
    a modulated signal source for generating an alternating current signal that is used to modulate said modulatable SPR sensor and thus change the shape of the SPR peak generated by the light incident on said modulatable SPR sensor; and
    a data processing system for recording the corresponding relationship between the incident angle and the intensity of the filtered reflected light and further obtaining the resonance angle of said modulatable SPR sensor.

2. The detection system for acquiring the SPR angle as recited in claim 1, characterized in that said alternating current signal is a periodic alternating current signal with a certain frequency.

3. The detection system for acquiring the SPR angle as recited in claim 2, characterized in that the passband central frequency of the narrowband filter system is the same as the frequency of the alternating current signal.

4. The detection system for acquiring the SPR angle as recited in claim 1, characterized in that said alternating current signal comprises a sine signal, a cosine signal, a triangular signal or a square wave signal.

5. The detection system for acquiring the SPR angle as recited in claim 1, characterized in that said data processing system is further used to obtain a position where the intensity of said reflected light is zero via straight line fitting according to the corresponding relationship between said incident angle and the intensity of the filtered reflected light, the incident angle corresponding to this position being determined as the resonance angle of said modulatable SPR sensor.

6. The detection system for acquiring the SPR angle as recited in claim 1, characterized in that said narrowband filter system may adopt a passive narrowband filter, a phase-locked amplifier, or a system consisting of an analog-to-digital converter and a digital signal processing filter; said modulatable SPR sensor is able to excite the surface plasma resonance effect and its generating condition for the SPR effect can be changed by the modulated input signal.

7. A method for acquiring the SPR angle, comprising the steps of:
  (1) forming a layer to be detected on the surface plasmon function layer of a modulatable SPR sensor to be detected;
  (2) directing a light, with a single wavelength and the polarization state being a transverse magnetic wave, incident on said modulatable SPR sensor;
  (3) modulating said modulatable SPR sensor and thus changing the shape of the SPR peak generated by the light incident on said modulatable SPR sensor by using an alternating current signal generated by a modulated signal source;
  (4) acquiring the intensity of the reflected light filtered by a narrowband filter system under different incident angles; and
  (5) obtaining the resonance angle of said modulatable SPR sensor according to the corresponding relationship between the incident angle and the intensity of the filtered reflected light as acquired in step (4).

8. The method for acquiring the SPR angle as recited in claim 7, characterized in that in step (3), said alternating current signal is a periodic alternating current signal with a certain frequency; said step (3) further includes setting the passband central frequency of the narrowband filter system to the same frequency as that of the alternating current signal output from the modulated signal source.

9. The method for acquiring the SPR angle as recited in claim 7, characterized in that in step (3), said alternating current signal comprises a sine signal, a cosine signal, a triangular signal, or a square wave signal.

10. The method for acquiring the SPR angle as recited in claim 7, characterized in that step (5) further comprises obtaining a position where the intensity of said reflected light is zero via straight line fitting according to the corresponding relationship between said incident angle and the intensity of the filtered reflected light, the incident angle corresponding to this position being determined as the resonance angle of said modulatable SPR sensor.

* * * * *